United States Patent
Grossman et al.

(10) Patent No.: US 10,421,870 B2
(45) Date of Patent: *Sep. 24, 2019

(54) COMPOSITION AND METHOD TO FORM A SELF DECONTAMINATING SURFACE

(71) Applicant: Allied Bioscience, Inc., Dallas, TX (US)

(72) Inventors: Craig Grossman, Point Roberts, WA (US); Mai Ngo, Tucson, AZ (US); Ronald Wysocki, Tucson, AZ (US)

(73) Assignee: ALLIED BIOSCIENCE, INC., Dallas, TX (US)

( * ) Notice: Subject to any disclaimer, the term of this patent is extended or adjusted under 35 U.S.C. 154(b) by 185 days.

This patent is subject to a terminal disclaimer.

(21) Appl. No.: 15/373,229

(22) Filed: Dec. 8, 2016

(65) Prior Publication Data

US 2017/0088717 A1 Mar. 30, 2017

Related U.S. Application Data

(63) Continuation of application No. 13/708,613, filed on Dec. 7, 2012, now Pat. No. 9,528,009, which is a continuation-in-part of application No. 13/448,325, filed on Apr. 16, 2012, now Pat. No. 9,757,769.

(60) Provisional application No. 61/489,630, filed on May 24, 2011, provisional application No. 61/476,233, filed on Apr. 15, 2011.

(51) Int. Cl.
*C09D 5/16* (2006.01)
*C09D 5/14* (2006.01)
*A01N 59/16* (2006.01)

(52) U.S. Cl.
CPC ........... *C09D 5/1618* (2013.01); *A01N 59/16* (2013.01); *C09D 5/14* (2013.01)

(58) Field of Classification Search
CPC ........ C09D 5/1618; C09D 5/14; A01N 37/36; A01N 59/16
See application file for complete search history.

(56) References Cited

U.S. PATENT DOCUMENTS

| | | | |
|---|---|---|---|
| 4,721,511 A | 1/1988 | Kupits | |
| 5,569,732 A | 10/1996 | Nohr et al. | |
| 6,037,289 A | 3/2000 | Chopin et al. | |
| 6,180,548 B1 | 1/2001 | Taoda et al. | |
| 6,228,480 B1 | 5/2001 | Kimura et al. | |
| 6,432,191 B2 | 8/2002 | Schutt | |
| 6,436,085 B1 | 8/2002 | Lauer | |
| 7,262,158 B1 | 8/2007 | Lukenbach et al. | |
| 7,541,048 B2 | 6/2009 | DeWitt et al. | |
| 7,763,565 B2 | 7/2010 | Fu et al. | |
| 2003/0127207 A1 | 7/2003 | Clark et al. | |
| 2004/0023824 A1 | 2/2004 | Zuechner et al. | |
| 2005/0008613 A1 | 1/2005 | Peterson et al. | |
| 2005/0008763 A1 | 1/2005 | Schachter | |
| 2005/0214483 A1 | 9/2005 | Fujieda et al. | |
| 2007/0065475 A1 | 3/2007 | Elfersy | |
| 2007/0167551 A1 | 7/2007 | Goodwin et al. | |
| 2007/0275101 A1 | 11/2007 | Lu | |
| 2008/0305153 A1 | 12/2008 | Wang et al. | |
| 2009/0062111 A1 | 3/2009 | Fu et al. | |
| 2009/0118152 A1 | 5/2009 | Lam et al. | |
| 2009/0209665 A1 | 8/2009 | Fu et al. | |
| 2009/0274914 A1 | 11/2009 | Hoshi et al. | |
| 2009/0298967 A1 | 12/2009 | Taylor et al. | |
| 2010/0028462 A1 | 2/2010 | Bolkan | |
| 2010/0055028 A1 | 3/2010 | Scott et al. | |
| 2010/0075298 A1 | 3/2010 | Creek et al. | |
| 2010/0144518 A1 | 6/2010 | Scott et al. | |
| 2010/0267550 A1 | 10/2010 | Fu et al. | |
| 2010/0292185 A1* | 11/2010 | Burns | A61K 31/69 514/64 |
| 2011/0274767 A1* | 11/2011 | Kato | B01J 13/0047 424/617 |
| 2012/0291667 A1 | 11/2012 | Geoffrion et al. | |
| 2013/0122074 A1* | 5/2013 | Kerrod | B01J 21/063 424/411 |

FOREIGN PATENT DOCUMENTS

| | | |
|---|---|---|
| CN | 1538937 | 10/2004 |
| CN | 101827650 | 9/2010 |
| CN | 101998979 | 3/2011 |
| EP | 0923988 | 9/2008 |
| KR | 1019990028236 | 4/1999 |
| KR | 1019990044670 | 6/1999 |
| KR | 1020080093483 | 10/2008 |
| KR | 1020080110268 | 12/2008 |
| KR | 1020090110672 | 10/2009 |
| KR | 1020100080509 | 7/2010 |

(Continued)

OTHER PUBLICATIONS

Notice of Allowance dated May 10, 2018 in U.S. Appl. No. 15/432,363.
Notice of Allowance dated May 11, 2018 in U.S. Appl. No. 15/432,352.
First Examination Report dated Jun. 21, 2018 in Indian Application No. 2084/MUMNP/2013.
Final Office Action dated May 4, 2017 in U.S. Appl. No. 13/448,325.
Notification of Reexamination dated May 25, 2017 in Chinese Application No. 201280026252.0.
Examination Report dated Jun. 2, 2017 in Australian Application No. 2017202598.
Examination Report dated Aug. 24, 2018 in European Application No. 12771919.3.

(Continued)

*Primary Examiner* — Samir Shah
(74) *Attorney, Agent, or Firm* — Snell & Wilmer L.L.P.

(57) ABSTRACT

A method to prepare a self-decontaminating surface, where that method includes dissolving tartaric acid in water, adding titanium (IV) isopropoxide to the tartaric acid solution to form a coating composition in water, and casting that coating composition onto a surface to form a coating having antimicrobial function.

7 Claims, 2 Drawing Sheets

(56) References Cited

FOREIGN PATENT DOCUMENTS

| WO | WO 2009029856 | 3/2009 |
|---|---|---|
| WO | WO 2009057046 | 5/2009 |

OTHER PUBLICATIONS

Grossman, et al., U.S. Appl. No. 15/968,586, filed May 1, 2018, entitled "Wet Wipes Comprising Antimicrobial Coating Compositions".
Communication Pursuant to Article 94(3) EPC dated Apr. 11, 2018 in European Application 12771919.3.
Notice of Preliminary Rejection dated Mar. 13, 2018 in Korean Application No. 10-2013-7030183.
2nd Office Action dated Mar. 5, 2018 in Mexican Application No. MX/a/2013/012000.
Office Action dated Feb. 20, 2018 in Canadian Application No. 2,833,177.
International Search Report and Written Opinion dated Jul. 17, 2012 in Application No. PCT/US2012/033844.
Restriction Requirement dated Apr. 17, 2013 in U.S. Appl. No. 13/708,613.
Restriction Requirement dated Oct. 2, 2013 in U.S. Appl. No. 13/448,325.
International Preliminary Report on Patentability dated Oct. 15, 2013 in Application No. PCT/US2012/033844.
Office Action dated Nov. 19, 2013 in U.S. Appl. No. 13/448,325.
International Search Report and Written Opinion dated Mar. 26, 2014 in Application No. PCT/US2013/073878.
Office Action dated Apr. 8, 2014 in U.S. Appl. No. 13/708,613.
Final Office Action dated Sep. 17, 2014 in U.S. Appl. No. 13/448,325.
Office Action dated Oct. 24, 2014 in U.S. Appl. No. 13/708,613.
Extended European Search Report dated Oct. 28, 2014 in European Application No. 12771919.3.
Office Action dated Dec. 11, 2014 in Chinese Application No. 201280026252.0.
Final Office Action dated Mar. 17, 2015 in U.S. Appl. No. 13/708,613.
Office Action dated Mar. 27, 2015 in U.S. Appl. No. 13/448,325.
International Preliminary Report on Patentability dated Jun. 9, 2015 in Application No. PCT/US2013/073878.
Office Action dated Aug. 4, 2015 in Chinese Application No. 201280026252.0.
Office Action dated Sep. 3, 2015 in U.S. Appl. No. 13/708,613.
Office Action dated Oct. 20, 2015 in U.S. Appl. No. 13/448,325.
Office Action dated Feb. 6, 2016 in Chinese Application No. 201280026252.0.
Office Action dated Mar. 17, 2016 in Russian Application No. 2013150917.
Final Office Action dated Jun. 1, 2016 in U.S. Appl. No. 13/708,613.
Patent Examination Report No. 1 dated Jun. 3, 2016 in Australian Application No. 2012242454.
Rejection Decision dated Jul. 6, 2016 in Chinese Application No. 201280026252.0.
Office Action dated Jul. 15, 2016 in Russian Application No. 2013150917.
Notice of Allowance dated Oct. 31, 2016 in U.S. Appl. No. 13/708,613.
Office Action dated Jan. 26, 2017 in U.S. Appl. No. 13/448,325.
Notice of Acceptance dated Feb. 8, 2017 in Australian Application No. 2012242454.
AEGIS, Mater Label—AEM 5772-5 Antimicrobial—A Silane Quaternary Ammonium Salt, 9 pages, 2006.
AEGIS, AEM 5772-5 Antimicrobial—A Silane Quaternary Ammonium Salt, 1 page, 2009.
AGIS Environments, "Material Safety Data Sheet," AEM 5772 Antimicrobial (72% Active Concentrate), pp. 1-7, USA, 2004.
Su et al., "Sol-gel preparation and photocatalysis of titanium dioxide," Catalysis Today 96, 2004, pp. 119-126, Elsevier B.V.
Liu et al., "Synthesis and Characterization of Titania Prepared by Using a Photoassisted Sol-Gel Method," Langmuir 2003, pp. 3001-3005.
Notice of Acceptance dated Jun. 28, 2017 in Australian Application No. 2017202598.
Notice of Allowance dated Jul. 13, 2017 in U.S. Appl. No. 13/448,325.
Grossman, et al., U.S. Appl. No. 15/432,334 filed Feb. 14, 2017 and entitled "Methods of Preparing Self-Decontaminating Surfaces Using Quaternary Silanes and Titanium Anatase Sol".
Grossman, et al., U.S. Appl. No. 15/432,352 filed Feb. 14, 2017 and entitled "Coating Compositions Comprising Polymers Having Titanium/Oxygen or Silicon/Oxygen Backbones".
Grossman, et al., U.S. Appl. No. 15/432,363 filed Feb. 14, 2017 and entitled "Methods of Preparing Reactive Mixtures of Quaternary Silanes and Titanium(IV)Alkoxides and Polymers Therefrom".
Decision to Grant dated Feb. 14, 2017 in Russian Application No. 2013150917/05.
Notice of Allowance dated Oct. 5, 2017 in U.S. Appl. No. 15/432,334.
Non-Final Office Action dated Oct. 6, 2017 in U.S. Appl. No. 15/432,352.
Non-Final Office Action dated Oct. 10, 2017 in U.S. Appl. No. 15/432,363.
Office Action dated Jun. 23, 2017 in Mexican Application No. MX/a/2013/012000.
EP Examindation Report dated Aug. 10, 2017 in EP Application No. 12771919.3.
Final Office Action dated Sep. 18, 2018 in Korean Application No. 10-2013-7030183.
Office Action dated Sep. 21, 2018 in Canadian Application No. 2,833,177.
Office Action dated Oct. 5, 2018 in Mexican Application No. MX/a/2013/012000.
Notice of Allowance dated Nov. 19, 2018 in Korean Application No. 10-2013-7030183.
Office Action dated Dec. 7, 2019 in Indonesia Application No. Wo0201305330.
Notice of Allowance dated Jan. 9, 2019 in Canadian Patent Application No. 2,833,177.

\* cited by examiner

OPTICAL IMAGE USING TRANSMISSION GEOMETRY WITH 10x OBJECTIVE
IMAGE SIZE: 2.4mm x 1.8 mm

COMPOSITION AND METHOD TO FORM A SELF DECONTAMINATING SURFACE

CROSS-REFERENCE TO RELATED APPLICATIONS

This application is a continuation of, claims priority to and the benefit, of U.S. Ser. No. 13/708,613 filed on Dec. 7, 2012 and entitled "COMPOSITION AND METHOD TO FORM A SELF DECONTAMINATING SURFACE." The '613 application is a continuation-in-part of, claims priority to and the benefit, of U.S. Ser. No. 13/448,325 filed on Apr. 16, 2012 and entitled "COMPOSITION AND METHOD TO FORM A SELF DECONTAMINATING SURFACE." The '325 application claims priority to and the benefit of U.S. Provisional Application No. 61/489,630 filed on May 24, 2011 and entitled "COMPOSITION AND METHOD TO FORM A SELF DECONTAMINATING SURFACE" and U.S. Provisional Application No. 61/476,233 filed on Apr. 15, 2011 and entitled "COMPOSITION AND METHOD TO FORM A SELF DECONTAMINATING SURFACE." All of the aforementioned applications are hereby incorporated by reference in their entirety.

FIELD

Embodiments generally relate a chemical composition and a method to form a self decontaminating surface. In certain embodiments, the chemical composition comprises a photocatalyst. In certain embodiments, the photocatalyst comprises a titanium oxide moiety.

BACKGROUND

Titanium oxide (e.g., $TiO_2$) is a nontoxic substance widely used in paints, paper, plastics, and toothpaste. It is known in the art that an alkali hydroxide can be added to an aqueous titanium salt solution to produce an amorphous titanium peroxide sol. The titanium peroxide sol can be reacted with an aqueous hydrogen peroxide solution to produce an amorphous titanium peroxide sol, which is then heated to high temperatures to obtain anatase titanium oxide.

Current methods for preparing sheets, coatings, or films comprising titanium oxide require that the titanium oxide particles be sintered at high temperatures (e.g., 200 to 400 degrees Celsius) in order to firmly support the titanium oxide on a substrate. Using these prior art methods, a titanium oxide compound is deposited onto a substrate, and then baked at approximately 200-400 degrees Celsius to fixedly set the compound on the substrate. The requirement of such high temperatures to cure the titanium oxide limits its utility, such as use of titanium dioxide to create self-decontaminating surfaces by retailers or consumers.

Accordingly, it would be an advance in the art to develop or use a new titanium oxide sheet, coating, or film deposition.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION

Figure 1:
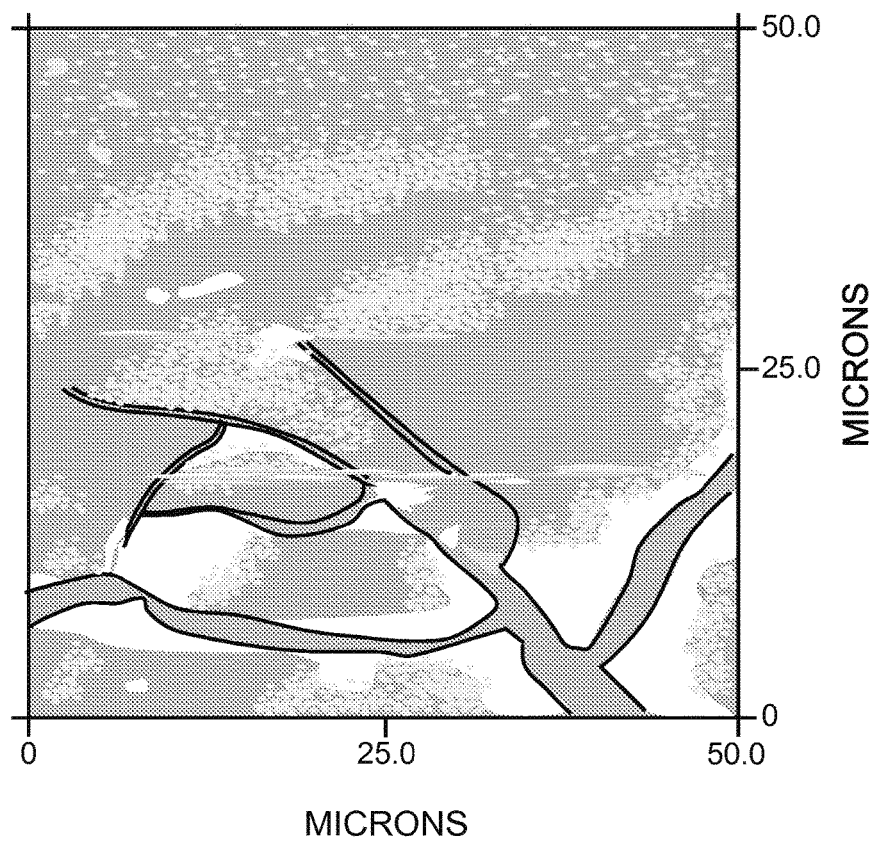
FIG. 1 is an Atomic Force Microscope image at 50 microns showing a coating on a glass surface, where that coating was formed using Applicants' composition and method.

The invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Titanium dioxide occurs in nature as well-known minerals rutile, anatase and brookite, and additionally as two high pressure forms, a monoclinic baddeleyite-like form and an orthorhombic α-PbO2-like form, both found recently at the Ries crater in Bavaria. The most common form is rutile, which is also the most stable form. Anatase and brookite both convert to rutile upon heating. Rutile, anatase and brookite all contain six coordinated titanium.

Titanium dioxide has numerous modifications—in addition to rutile, anatase and brookite there are three metastable forms produced synthetically (monoclinic, tetragonal and orthorombic), and high pressure forms (α-PbO2-like, baddeleyite-like and cotunnite-like):

Oxidation—loss of electrons or an increase in oxidation state by a molecule, atom or ion.

Substances that have the ability to oxidize other substances are said to be oxidative or oxidizing and are known as oxidizing agents, oxidants, or oxidizers. Put another way, the oxidant removes electrons from another substance, and is thus itself reduced. And, because it "accepts" electrons, it is also called an electron acceptor.

In chemistry, photocatalysis is the acceleration of a photoreaction in the presence of a catalyst.

In catalyzed photolysis, light is absorbed by an adsorbed substrate. In photogenerated catalysis, the photocatalytic activity (PCA) depends on the ability of the catalyst to create electron-hole pairs, which generate free radicals (hydroxyl radicals: .OH) able to undergo secondary reactions. Its comprehension has been made possible ever since the discovery of water electrolysis by means of the titanium dioxide. Commercial application of the process is called Advanced Oxidation Process (AOP). There are several methods of achieving AOP's, that can but do not necessarily involve $TiO_2$ or even the use of UV light. Generally the defining factor is the production and use of the hydroxyl radical.

When $TiO_2$ is illuminated with light of sufficient energy, electron-hole pairs are excited so that additional electrons go across the band gap to conduction band ("CB"), while holes stay in the valence band ("VB"). The excited electrons may then be used for redox reactions at the surface of $TiO_2$. There are multiple phases of $TiO_2$. For example, Rutile phase can be excited by visible light, but has a fast charge recombination rate; Anatase, on the other hand, has a slow recombination rate, but can only be excited by UV lights. Thus, it is reasonable to produce mixed phase photocatalyst to increase the total efficiency Certain titanium oxide crystalline morphologies exhibit photocatalytic characteristics when exposed to Ultra Violet (UV) light. When exposed to UV light, titanium oxide, creates electron-hole pairs which generate free radical (e.g., hydroxyl radicals). The degree of photocatalytic strength varies depending on the type of titanium oxide, for example anatase titanium oxide (particle size of about 5 to 30 nanometers) is a stronger photocatalyst than rutile titanium oxide (particle size of about 0.5 to 1 microns). Therefore, titanium oxide has potential use in sterilization, sanitation, and remediation applications.

In certain embodiments, Applicants' method and composition provide a titanium alkoxide starting material $(RO)_4Ti$ photocatalyst surface coating precursor. For example, in certain embodiments Applicants' method forms a liquid coating composition using titanium tetraisopropoxide 1.

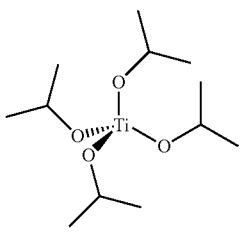

In certain embodiments, that liquid coating composition is cast onto a surface to form a coating comprising a linear polymeric structure 3 on the surface.

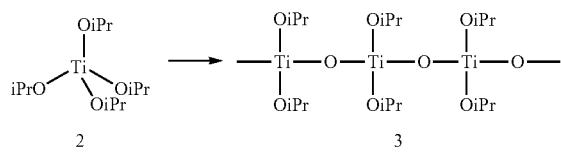

In other embodiments, Applicants' method forms a liquid coating composition using titanium tetraisopropoxide 2, and casts that coating composition solution onto a surface to form a coating comprising a cross-linked structure 4 on the surface.

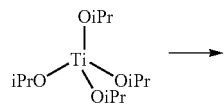

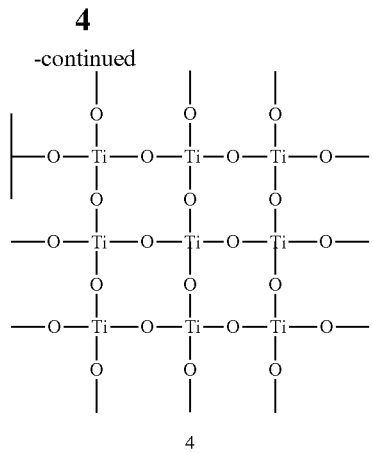

In other embodiments, Applicants' coating composition is formed using titanium tetraisopropoxide The following Example is presented to further illustrate to persons skilled in the art how to make and use the invention. This example is not intended as a limitation, however, upon the scope of the invention.

Example 9.0 grams of tartaric acid were dissolved in 0.120 liters of water in an Erlynmeyer flask to give a 0.5 molar solution. This solution was stirred overnight at room temperature. The following day, the tartaric acid solution was filtered through filter paper (Whatman #1), then subsequently through a 0.2 micron PRFW filter to remove particulates. 25 mL of filtered 0.5 M tartaric acid (0.01249 moles of tartaric acid) was poured into a round bottom flask and chilled on ice with stirring. 3.69 grams of titanium (IV) isopropoxide was added slowly first with a 1 mL addition. 1 mL aliquots of titanium (IV) isopropoxide were added until all of it was added to the tartaric acid solution.

Upon addition of the titanium (IV) isopropoxide the ice bath was removed. The solution remained a solution for approximately 10 minutes after which it became a clear gel and became progressively opaque (white). The gel was stirred at RT overnight. The gelatinous material was mixed with water, or alcohol ROH and water, and then cast onto a glass slide to form a coating thereon.

Depending on the stoichiometry of the starting materials, in certain embodiments Applicants' coating of this Example comprises a tartaric acid/titanium isopropoxide adduct 5, wherein R is H, alkyl, and phenyl. When the molar ratio of $TI(OR)_4$ and tartaric acid is greater that about 3, the adduct product 5 predominates.

When the molar ratio of $TI(OR)_4$ and tartaric acid is about 1, A polymeric product 6 predominates, wherein (r) is between 2 and about 10. When the molar ratio of $TI(OR)_4$ and tartaric acid is greater than 1 but less than about 3, a mixture of adduct 5 and polymer 6 is obtained. In the Example, the molar ratio is about 5, and adduct 5 is predominately formed.

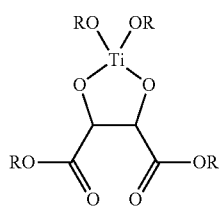

-continued

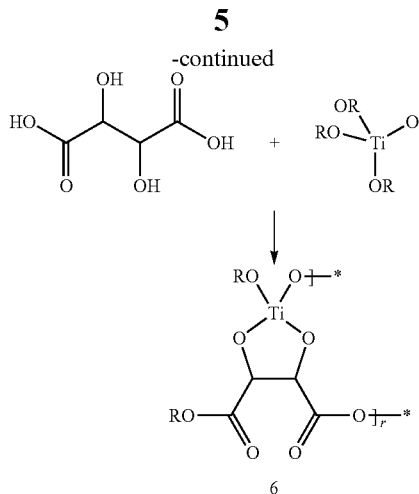

In other embodiments, Applicants' coating composition comprises one or more hydroxyl acids other than tartaric acid in combination with $TiO_2$. In certain embodiments, these one or more hydroxyl acids include one or more alpha hydroxyl acids including glycolic acid, lactic acid, citric acid, and/or mandelic acid. In certain embodiments, these one or more hydroxyl acids include one or more beta hydroxyl acids including salicyclic acid and/or beta-hydroxypropionic acid.

Figure 2:
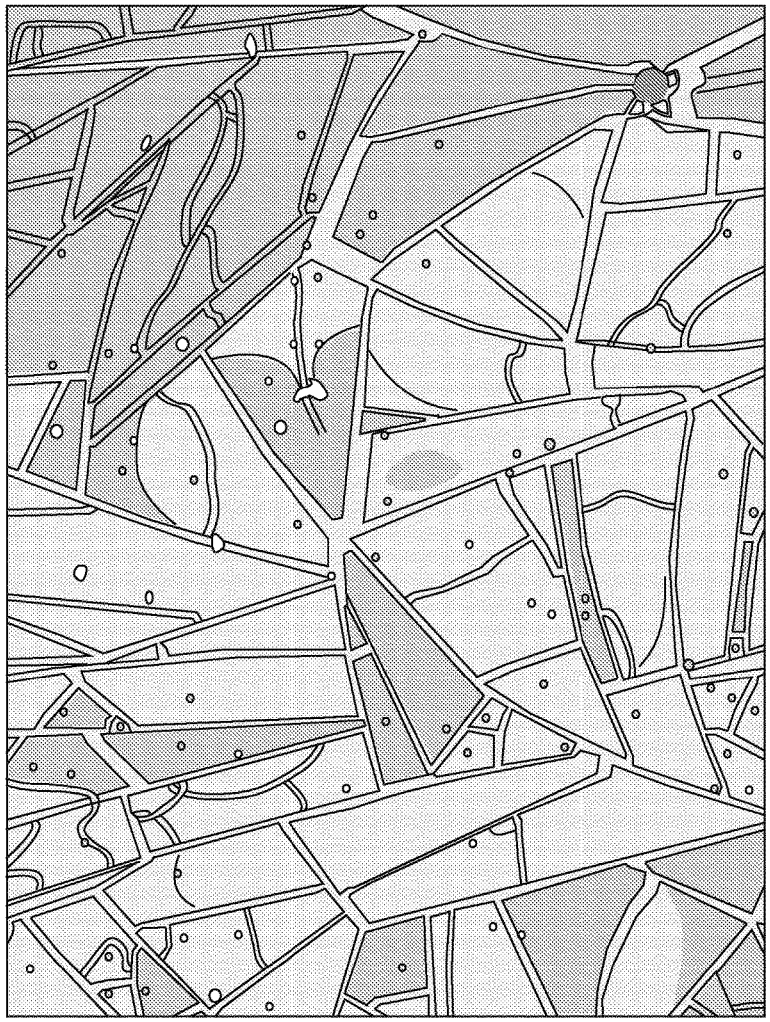
FIG. 2 is an optical image using transmission geometry with 10× objective showing a coating on a glass surface, where that coating was formed using Applicants' composition and method.

FIGS. 1 and 2 show images of the coating formed on the glass surface. FIG. 1 is an Atomic Force Microscope image at 50 microns. FIG. 2 is an optical image using transmission geometry with 10× objective.

In certain embodiments, Applicants' coating composition is embodied in a flexible, planar member to form a composite disinfecting wipe. Applicants' composite disinfecting wipe is capable of cleaning and removing residues from soiled surfaces while simultaneously destroying undesirable microorganisms, e.g. bacteria, mold, viruses, prions and the like that colonize on common surfaces with which people come into contact, such as doorknobs, countertops, toilet seats, floors, beds, walls, and the like.

Glass slides prepared in accord with the Example were inoculated with bacteria or virus and sampled at various times with a sterile cotton swab. That cotton swab was placed into a tube containing a neutralizing broth. Methicillin resistant Staphylococcus aureus ("MRSA") and MS-2 were utilized. MS-2 is a bacteriophage used as a surrogate for Norovirus, Enterovirus, Polio, and the like. TABLE 1 recites log reduction of MRSA-inoculated glass slides coated using various weight percent solutions of the composition of the Example to form a coating on the glass slides prior to MRSA inoculation.

TABLE 1

Log Reductions of MRSA Using Composition Of Example

| Time Points | 10% | 5% | ~3% | ~1% |
|---|---|---|---|---|
| | | Log Reduction | | |
| 10 minutes | 1.0 | 0.9 | 0.4 | 0.3 |
| 1 Hour | Not Done | Not Done | >5.9 | 0.1 |
| 2 hours | >5.6 | >4.0 | >5.5 | 1.8 |

TABLE 2 recites data using slides coated using a 10 weight percent composition of the Example to form a coating on the glass slides prior to either MRSA or MS-2 inoculation. MS-2 was showed an average of 2.4 log reduction at two hours. MRSA showed greater than a 5.6 log reduction at two hours.

TABLE 2

Average Log Reduction For MRSA And MS-2 At Two Hours

| | 10 MINUTES | 2 HOURS |
|---|---|---|
| MS-2 | 0.6 | 2.4 |
| MRSA | 1.9 | >5.6 |

A test using glass slides coated using a 3 weight percent solution of the coating composition of the Example, and inoculated with either MRSA or MS-2, wherein the slides were inoculated in the dark, did not show any log reduction. This result shows that the titanium moieties in the glass slide coating were providing anti-microbial function via a photocatalytic effect.

TABLE 3 recites data regarding the anti-microbial efficacy of coatings formed on glass slides using various weight percent solutions of the coating composition of the Example.

TABLE 3

Log Reductions Of Organisms After 1 Hour

| Organism | 5% | ~3% | ~1% |
|---|---|---|---|
| | | Log Reduction | |
| MS-2 | 4.1 | 1.3 | 1.7 |
| E. coli | >5.0 | >5.0 | >5.0 |
| Ps. aeruginosa | >5.2 | >5.2 | >5.2 |

While the preferred embodiments of the present invention have been illustrated in detail, it should be apparent that modifications and adaptations to those embodiments may occur to one skilled in the art without departing from the scope of the present invention as set forth herein.

We claim:

1. A self-decontaminating coating disposed on a surface, formed by the method consisting of:
dissolving tartaric acid in water to form a tartaric acid solution;
forming an opaque gel by adding titanium (IV) isopropoxide to the tartaric acid solution to form an 18 weight percent loading of tartaric acid and titanium (IV) isopropoxide in water;
diluting said gel with water to form a 10 weight percent loading of tartaric acid and titanium (IV) isopropoxide in water; and
casting the 10 weight percent aqueous gel onto a surface to form the self-decontaminating coating.

2. The self-decontaminating coating of claim 1, wherein the surface is glass.

3. The self-decontaminating coating of claim 1, wherein the self-decontaminating coating exhibits greater than a log 5.6 reduction in MRSA concentration 2 hours after inoculation of the self-decontaminating coating with an initial MRSA concentration.

4. A self-decontaminating coating disposed on a surface, formed by the method consisting of:
dissolving tartaric acid in water to form a tartaric acid solution;
forming an opaque gel by adding titanium (IV) isopropoxide to the tartaric acid solution to form an 18 weight percent loading of tartaric acid and titanium (IV) isopropoxide in water;

diluting said gel with water to form a 3 weight percent loading of tartaric acid and titanium (IV) isopropoxide in water; and casting the 3 weight percent aqueous gel onto a surface to form the self-decontaminating coating.

5. The self-decontaminating coating of claim 4, wherein the self-decontaminating coating exhibits greater than a log 5.5 reduction in MRSA concentration 2 hours after inoculation of the self-decontaminating coating with an initial MRSA concentration.

6. A self-decontaminating coating disposed on a surface, formed by the method consisting of:

dissolving tartaric acid in water to form a tartaric acid solution;

forming an opaque gel by adding titanium (IV) isopropoxide to the tartaric acid solution to form an 18 weight percent loading of tartaric acid and titanium (IV) isopropoxide in water;

diluting said gel with water to form a 1 weight percent loading of tartaric acid and titanium (IV) isopropoxide in water; and casting the 1 weight percent aqueous gel onto a surface to form the self-decontaminating coating.

7. The self-decontaminating coating of claim 6, wherein the self-decontaminating coating exhibits a log 1.8 reduction in MRSA concentration 2 hours after inoculation of the self-decontaminating coating with an initial MRSA concentration.

\* \* \* \* \*